(12) United States Patent
Özbal (10) Patent No.: US 7,100,460 B2
(45) Date of Patent: Sep. 5, 2006

(54) CONCENTRIC TUBE MICROPLATE AUTOSAMPLE INTERFACE

(75) Inventor: Can Özbal, Cambridge, MA (US)

(73) Assignee: Biotrove, Inc., Woburn, MA (US)

( * ) Notice: Subject to any disclaimer, the term of this patent is extended or adjusted under 35 U.S.C. 154(b) by 90 days.

(21) Appl. No.: 10/821,124

(22) Filed: Apr. 8, 2004

(65) Prior Publication Data
US 2005/0223822 A1    Oct. 13, 2005

(51) Int. Cl.
*B01L 3/02*    (2006.01)
(52) U.S. Cl. .................................... 73/864.11
(58) Field of Classification Search .............. 73/61.52, 73/61.55, 61.56, 863.01, 864.01, 864.02, 73/864.15, 864.21, 864.87, 864.11
See application file for complete search history.

(56) References Cited
U.S. PATENT DOCUMENTS

| | | | | |
|---|---|---|---|---|
| 3,530,721 A * | 9/1970 | Jiri ............................ | 73/863.72 |
| 4,478,095 A | 10/1984 | Bradley et al. ........... | 73/864.21 |
| 4,577,514 A | 3/1986 | Bradley et al. ........... | 73/863.01 |
| 4,624,148 A | 11/1986 | Averette ................... | 73/864.21 |
| 5,400,923 A | 3/1995 | Golias et al. ................ | 222/82 |
| 5,614,154 A * | 3/1997 | Glatz et al. ................. | 422/103 |
| 6,146,594 A * | 11/2000 | De Graaff et al. .......... | 422/100 |
| 6,447,483 B1 * | 9/2002 | Steube et al. ............... | 604/158 |

FOREIGN PATENT DOCUMENTS

| | | |
|---|---|---|
| EP | 0 348 116 | 6/1989 |
| WO | WO 89/12829 | 12/1989 |
| WO | WO 92/00144 | 1/1992 |

OTHER PUBLICATIONS

International Search Report dated Jun. 28, 2005.

* cited by examiner

*Primary Examiner*—Charles Garber
(74) *Attorney, Agent, or Firm*—Linda M. Buckley; Scott B. Weston; Edwards Angell Palmer & Dodge LLP (57) ABSTRACT

In accordance with an illustrative embodiment of the invention, a system for obtaining a fluidic sample from a container is presented. The container defines a volume for holding the sample, the volume being closed by a seal. An outer tube has a proximal end and a distal end, the proximal end shaped to permit piercing the seal. An inner tube has an end region axially movable within the outer tube between a piercing position, wherein an end of the inner tube in the end region is retracted from the proximal end of the outer tube, and a transmission position, wherein the end of the inner tube extends axially beyond the proximal end of the outer tube. The outer tube and the inner tube form a tube assembly. At least one of the tube assembly and the container can be moved to cause the outer tube to pierce the seal and, after the seal is pierced, the inner tube can be used in the transmission position to permit fluid transfer with respect to the volume.

27 Claims, 5 Drawing Sheets

CONCENTRIC TUBE MICROPLATE AUTOSAMPLE INTERFACE

TECHNICAL FIELD

The invention generally relates to techniques for assaying sample liquids, and more specifically to physical transfer of a small sample of fluid from a sealed volume.

BACKGROUND ART

High-throughput screening (HTS) is a method for the rapid and accurate analysis of large numbers of chemical compounds for activity against selected targets. Typical chemical libraries contain hundreds of thousands to millions of separate compounds that are screened against a wide variety of targets. The large numbers of assays that must be routinely screened has led to a requirement for new technologies capable of rapid and quantitative analysis of small amounts of fluidic samples.

Often, the small samples to be processed in HTS are initially stored in a plurality of small wells formed in a microplate. The microplate, which is typically made of polypropylene or other plastic, may vary in size, and include any number of wells. For example a standard microplate may have a dimension of 128 mm×86 mm×14 mm and include 96, 384, or 1536 wells, with each well having an opening diameter of 1–7 mm and a working volume of 3–300 µl.

After the samples are loaded in their respective well, the microplate is typically sealed, so as to preserve the sample. Preventing evaporation of the sample can be critical, especially when such small amounts of fluidic samples are involved. The seal may be a foil, such as aluminum foil, which may be attached to the plate via a pressure sensitive adhesive (PSA) and/or a heat seal. Once sealed, the microplate can be stored for incubation and/or transferred to a test site for further processing.

To further process the samples sealed in the microplate wells, it is often required to transfer a given sample from the microplate to an analyzer, such as a mass spectrometer and/or a chromatography column. This can be accomplished by puncturing the seal of a particular well and aspirating the sample from the well to the desired destination.

However, problems arise when attempting to remove the sample from its respective well. To aspirate the sample from the well, a tube having a small diameter compatible with the size of the well is required. If the tube is too flexible, such as a tube made of Teflon, the tube will not be able to puncture the seal covering the well. Instead, upon contacting the seal, the Teflon tube will simply bend.

Alternatively, a tube made of a material capable of puncturing the seal, such as stainless steel, often is not chemically compatible. A major concern in maximizing sample throughput is the elimination of sample-to-sample carryover. Stainless steel is not a particularly bio-inert substrate and tends to strongly adsorb hydrophobic compounds in its surface. Hence, prior to aspirating the next sample, a stainless steel syringe must be thoroughly washed to prevent carryover of sample. When dealing with a large number of samples, the additional time required to thoroughly wash the stainless steel syringe, compared to a syringe made of a bio-inert substrate, can become a time consuming limitation on the system. To minimize carryover, various hydrophobic surface coatings may be applied to the surface of the syringe, however the durability of these surface coatings is limited.

SUMMARY OF THE INVENTION

In accordance with an illustrative embodiment of the invention, a system for obtaining a fluidic sample from a container is presented. The container defines a volume for holding the sample, the volume being closed by a seal. An outer tube has a proximal end and a distal end, the proximal end shaped to permit piercing the seal. An inner tube has an end region axially movable within the outer tube between a piercing position, wherein an end of the inner tube in the end region is retracted from the proximal end of the outer tube, and a transmission position, wherein the end of the inner tube extends axially beyond the proximal end of the outer tube. The outer tube and the inner tube form a tube assembly. At least one of the tube assembly and the container can be moved to cause the outer tube to pierce the seal and, after the seal is pierced, the inner tube can be used in the transmission position to permit fluid transfer with respect to the volume.

In related embodiments of the invention, the inner tube is mechanically biased in the transmission position, such bias being normally overcome while the outer tube is used to pierce the seal. In various embodiments, when the inner tube is in the transmission position, the tube assembly can be moved relative to the container so as to cause the end of the inner tube to make contact with the seal and move the inner tube into the piercing position. In various embodiments, when the inner tube is in the piercing position, the inner tube returns to the transmission position after the seal is pierced due to the mechanical bias. The inner tube may have a second end that is fixed in position relative to the outer tube, the inner tube being resilient so as to cause the inner tube to be mechanically biased in the transmission position. The second end of the inner tube may extend beyond the distal end of the outer tube, with a portion of the inner tube positioned between the distal end of the outer tube and the second end of the inner tube flexing when in the inner tube is in the piercing position. The inner tube may be capable of moving freely within the outer tube.

In accordance with other related embodiments of the invention, a source of suction may be in fluid communication with the inner tube, the source of suction for aspirating the sample. An injection valve may be in fluid communication with the inner tube, the injection valve capable of selectively placing the source of suction in fluid communication with the inner tube. The system may include an analyzer for determining a characteristic of the sample aspirated from the container, such as a chromatography column or a mass spectrometer. The outer tube and inner tube may be concentric. The outer tube may be made of a metal or a metal alloy. The inner tube may be made of a wide variety of materials that may be advantageously bioinert, including various plastics, such as polymide and Poly Ether Ether Ketone (PEEK). In various embodiments, the inner tube may be made of fused silica with a polymide sheath, or nitinol that may be coated with an appropriate hydrophobic coating. The inner tube may be made, without limitation, of a resilient, flexible, and/or elastic material.

In accordance with further related embodiments, the container may be a microplate. The microplate includes a plurality of wells, each well for holding a sample and closed by a seal. A controller may control movement of at least one of the tube assembly and the container. A mount may permit motion of the tube assembly relative to the container.

In accordance with another aspect of the invention, a method for obtaining a fluidic sample from a sealed container using a tube assembly is presented. The container defines a volume for holding the sample, the volume closed by a seal. The tube assembly includes an outer tube having a proximal end shaped to permit piercing the seal. The tube assembly further includes an inner tube having an end region axially movable within the outer tube. The inner tube is placed in a piercing position, wherein an end of the inner tube is retracted from the proximal end of the outer tube. The seal is pierced with the proximal end of the outer tube. The inner tube is then placed in a transmission position, wherein an end of the inner tube in the end region extends axially beyond the proximal end of the outer tube.

In related embodiments of the invention, a source of suction is applied to the inner tube to aspirate the sample fluid from the volume. The aspirated sample fluid may then be analyzed using, for example, chromatography and/or mass spectrometry. Applying a source of suction to the inner tube may include applying a source of suction to the inner tube via an injection valve. The container may be a microplate that includes a plurality of wells, each well for holding a sample and closed by a seal, wherein the method further includes moving at least one of the tube assembly and the container so as to aspirate sample from each well.

In further related embodiments of the invention, the inner tube may mechanically biased in the transmission position, such that placing the inner tube in the piercing position includes overcoming the mechanical bias. The inner tube may be resilient, and placing the inner tube in the piercing position includes flexing a portion of the inner tube. The inner tube may thus return to the transmission position due to the resiliency of the inner tube. Placing the inner tube in the piercing position may include moving at least one of the tube assembly and the container such that the end of the inner tube contacts the seal and moves into the piercing position.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a system and method for transferring a sample from a volume closed by a seal is presented. Generally, the system includes a tube assembly having an outer tube and an inner tube. The inner tube includes an end region axially movable within the outer tube, such that the outer tube can be used to pierce the seal, while the inner tube can be used for contacting and transferring the sample from the volume. Consequently, the inner tube can advantageously have a small diameter and be made of a bio-inert substrate that, while not capable of piercing the seal, adsorbs very little sample. Sample carryover and the time required to wash the tubing prior to transfer of the next sample can thus be minimized. Details are discussed below.

Figure 1:
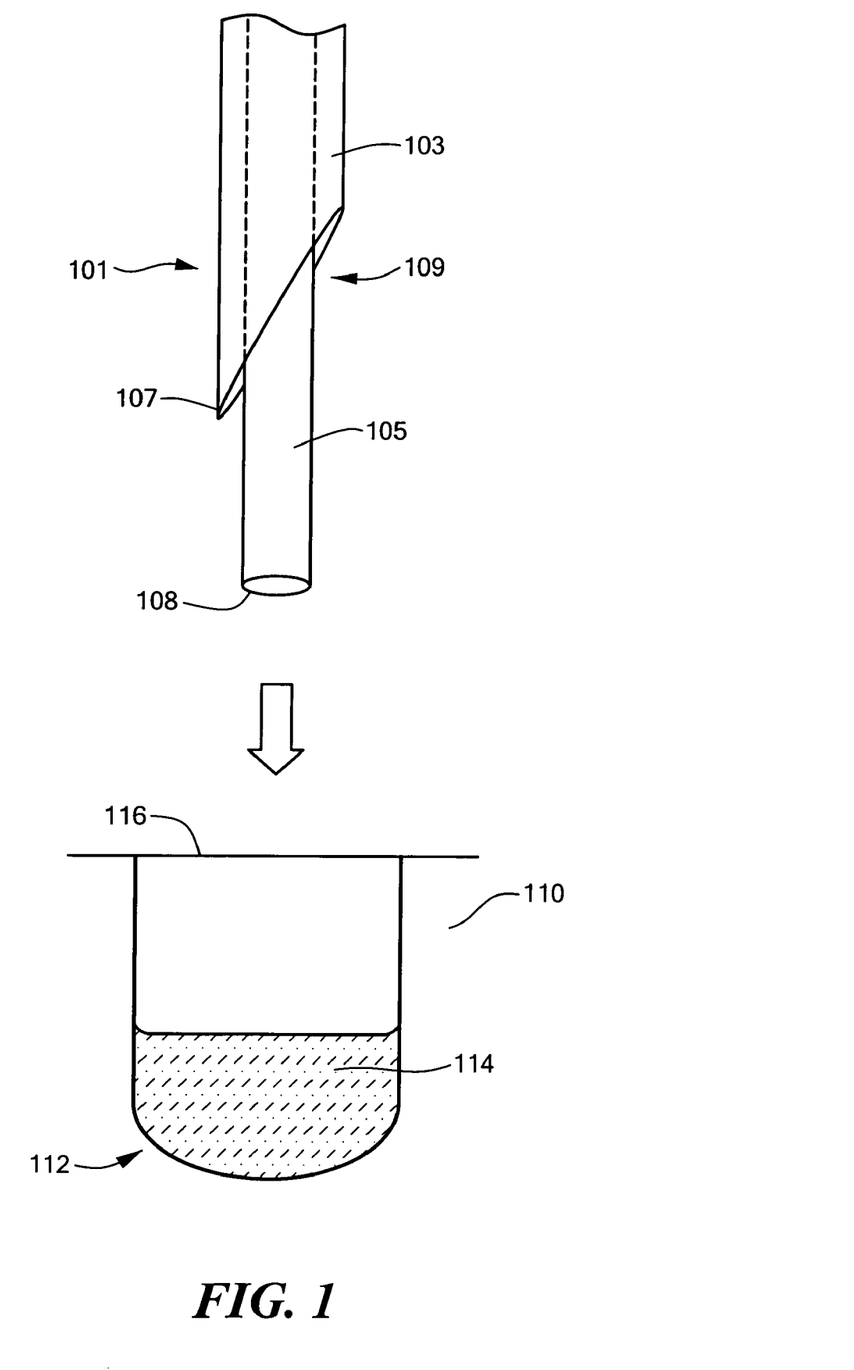
FIG. 1 is a diagram illustrating a tube assembly approaching a container, the container including a volume closed by a seal, in accordance with one embodiment of the invention.

FIG. 1 shows a tube assembly 101 approaching a container 110, in accordance with one embodiment of the invention. The container 110 defines at least one volume capable of containing a sample 114 to be aspirated. In various embodiments, the container 110 may be a standard microplate that includes a plurality of small wells 112, as described above. For example, the microplate may have a dimension of 128 mm×86 mm×14 mm and include, without limitation, 96, 384, or 1536 wells having an opening well diameter between 1–7 mm and working volumes of, approximately, 2 µl to 300 µl. In other embodiments, the container 110 may be a platen that includes a plurality of through-hole wells which transverse the platen, as described in, for example, U.S. Pat. No. 6,387,331 and U.S. patent application 20020094533, the contents of which are incorporated herein by reference.

The volume containing the sample 114 to be aspirated has an opening that is initially closed by a seal 116. The seal 116 helps to preserve and prevent evaporation of the sample 114. In various embodiments, the seal 116 is made of a foil, such as aluminum foil, or a plastic. The seal 116 may be attached to the container 110 via a pressure sensitive adhesive and/or the seal 116 may be a heat seal that is attached by applying heat. Typically, a single seal 116 covers each well of a given microplate.

In various embodiments of the present invention, the tube assembly 101 includes an outer tube 103 and an inner tube 105. At least a portion of the inner tube 105 is positioned within the outer tube 103, and may be, without limitation, concentric with the outer tube 103. The outer tube 103 is used to pierce the seal 116 and preferably does not contact the sample 114, while the inner tube 105 is used to aspirate the sample 114 from the volume.

The outer tube 103 includes a proximal end 107 that is shaped to permit piercing of the seal 116. For example, the proximal end 107 may be, without limitation, sharp and/or pointed. Alternatively, the proximal end 107 may be blunt, but sufficiently rigid to permit piercing the seal 116. The outer tube 103 may be made of a wide variety of materials capable of punching through the seal 116, such as, without limitation, various metals/alloys, such as stainless steel or titanium. Since the outer tube 103 does not contact the sample 114 in preferred embodiments, the material from which the outer tube 103 is made can be chosen without regard to sample 114 compatibility.

The outer diameter of the outer tube 103 is constrained by the dimensions of the opening closed by the seal 116. For example, in a 1536 well microplate, each well typically has an opening that is approximately 1 mm in diameter. The outer diameter of the outer tube 103 should thus be less than 1 mm, such that the proximal end 107 of the outer tube 103 can protrude into the well and pierce the seal 116. A portion of the inner tube 105 is positioned within the outer tube 103, and thus has an outer diameter less than the inner diameter of the outer tube 103. In an illustrative embodiment, the outer diameter of the inner tube 105 may be, for example, 360 microns, so as to be compatible with one or more valves (described in more detail below) connected to the inner tube 105.

A limitation on the inner diameter of the inner tube 105 is the ability to aspirate the sample 114 at a reasonable rate with the application of a vacuum. If a very narrow diameter inner tube 105 is used, the application of a vacuum at one end of the inner tube 105 will not be sufficient to aspirate the sample 114 through the inner tube 105 at an appreciable rate, thereby resulting in a decrease in system sample throughput. In illustrative embodiments, the inner diameter of the inner tube 105 ranges from, without limitation, 100 to 300 microns.

The inner tube 105 may be made of a wide variety of materials, such as various plastics, metals, and/or alloys. In various embodiments of the invention, the inner tube 105 may be made of a bio-inert material that adsorbs a minimal amount of the sample 114. Thus, sample carryover, and the time required to wash the inner tube 105 prior to aspirating the next sample, is minimized. Suitable bio-inert materials for the inner tube 108 include, without limitation, polymide and Poly Ether Ether Ketone (PEEK). Depending on the specific application, a coating may be applied to the surface of the inner tube 105. For example, a hydrophobic coating may be applied to the inner tube 105, particularly when the inner tube 105 is made of a non bio-inert material (however, as described above, the durablility of the coating may be somewhat limiting). Further limitations on the material used for the inner tube 105, such as a desired flexibility and/or resiliency, may also be imposed, as described in more detail below. Due to the small diameter and the application specific material chosen for the inner tube 105, the inner tube 105 is often incapable of piercing the seal 116. Upon contacting the seal 116, the inner tube will often flex and/or break, thus entailing the use of the outer tube 103 for piercing the seal 116.

The inner tube 105 includes an end region 109 axially movable within the outer tube 105 between a transmission position, as illustrated in FIG. 1, and a piercing position (see FIG. 2, described below). In the transmission position, an end 108 of the inner tube 105 in the end region 109 extends axially beyond the proximal end 107 of the outer tube 103. The tube assembly 101 and/or the container 110 can thus be moved so that the inner tube 105, and not the outer tube 103, makes contact with the sample 114.

Figure 2:
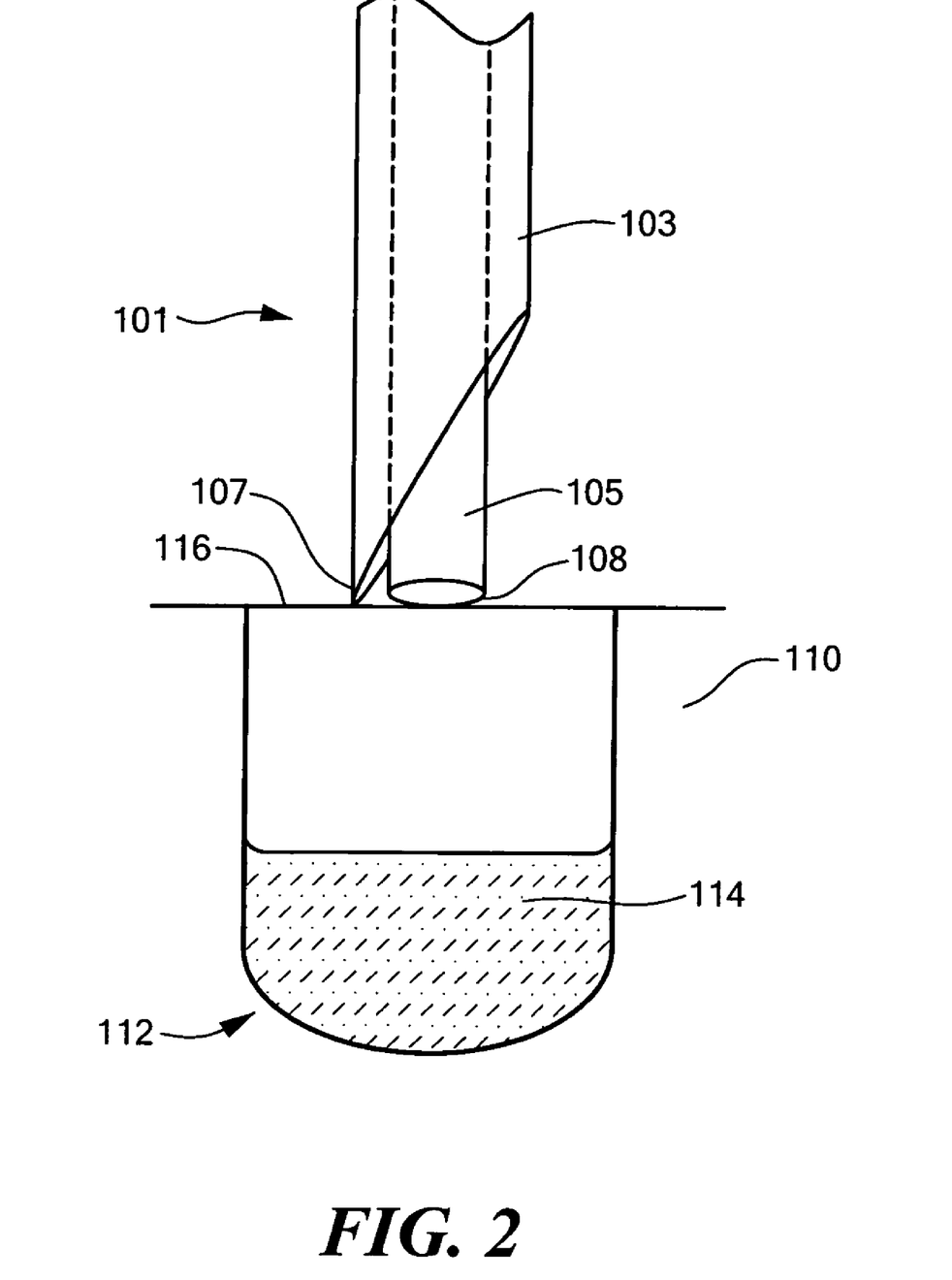
FIG. 2 is a diagram illustrating the tube assembly of FIG. 1 in a piercing position, in accordance with one embodiment of the invention.

FIG. 2 is a diagram illustrating the tube assembly 101 of FIG. 1 in the piercing position, in accordance with one embodiment of the invention. In the piercing position, the end 108 of the inner tube 105 is retracted from the proximal end 107 of the outer tube 103. Thus, while in the piercing position, the tube assembly 101 and/or the container 110 can be moved so as to cause the proximal end 107 of the outer tube 103 to pierce the seal 116.

Figure 3:
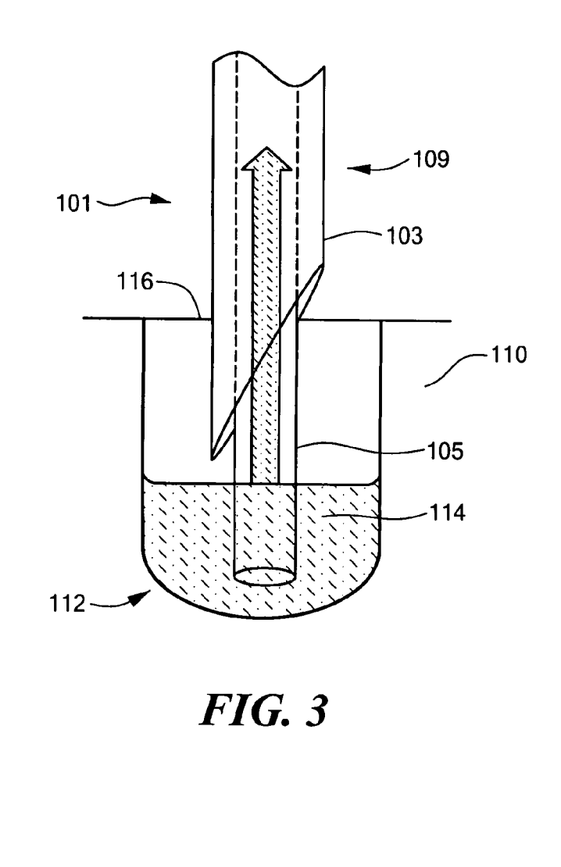
FIG. 3 is a diagram illustrating the tube assembly of FIG. 1 after penetrating the seal, in accordance with one embodiment of the invention.
Figure 4:
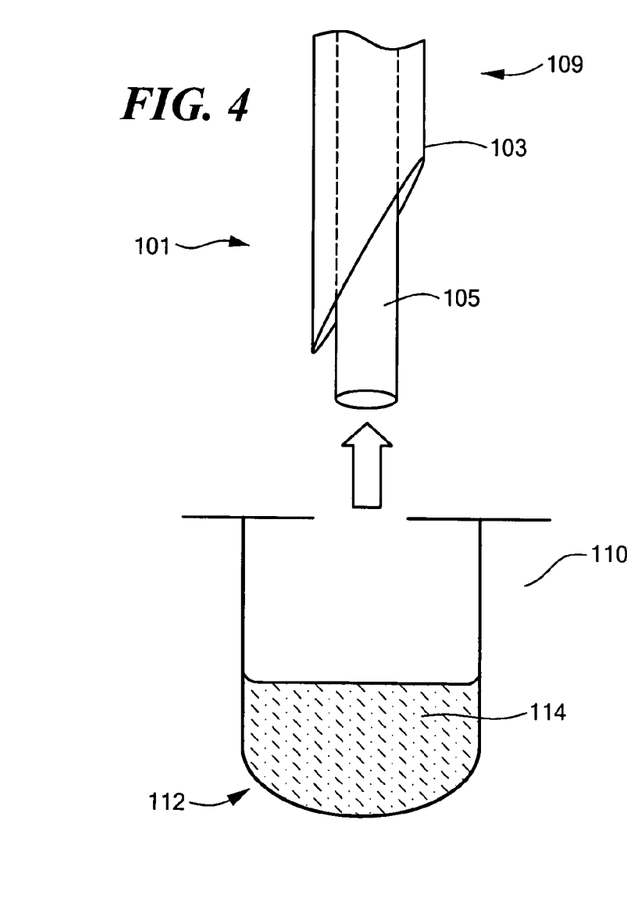
FIG. 4 is a diagram illustrating the tube assembly of FIG. 2 moving away from the container, in accordance with an embodiment of the invention.

FIG. 3 is a diagram illustrating the tube assembly 101 of FIG. 1 in the transmission position after the seal 116 has been penetrated, in accordance with one embodiment of the invention. After the outer tube 103 has pierced the seal 116, the tube assembly 101 is moved to the transmission position, and if necessary, the tube assembly 101 and/or the container 110 moved, such that the end 108 of the inner tube 105 makes contact with the sample. To minimize carryover of sample 114, the inner tube 105 protrudes a desired distance from the outer tube 103 so that that outer tube 103 does not contact the sample 114 in the volume. The sample 114 can then be aspirated, or otherwise transferred, from the container 112 via the inner tube 105.

After the sample 114 has been transferred from the container 112, the tube assembly 101 and/or the container 110 can be moved so as to retract the tube assembly 108 from the opening. The inner tube 105 may then be washed of any sample carryover by, without limitation, aspirating a washing solution through the inner tube 105. The tube assembly 101 is then ready to transfer another sample.

In various embodiments of the invention, the inner tube 105 is mechanically biased in the transmission position, such bias being normally overcome while the tube assembly 101 is in the piercing position. The mechanical bias may be based, for example, on the resiliency of the inner tube, as described in more detail below. In other embodiments of the invention, the bias mechanism may include other suitable means known in the art, such as a spring mechanism.

The mechanical bias may be overcome, for example, by moving the tube assembly 101 and the container 110 towards each other, as shown in FIG. 1. It is to be understood that either or both the tube assembly 101 and the container 110 can be moved. The inner tube 105 will make contact with the seal 116, and, in overcoming the bias, move into the piercing position, as shown in FIG. 2. After the outer tube 103 pierces the seal 116, the bias returns the tube assembly 101 to the transmission position.

Figure 5:
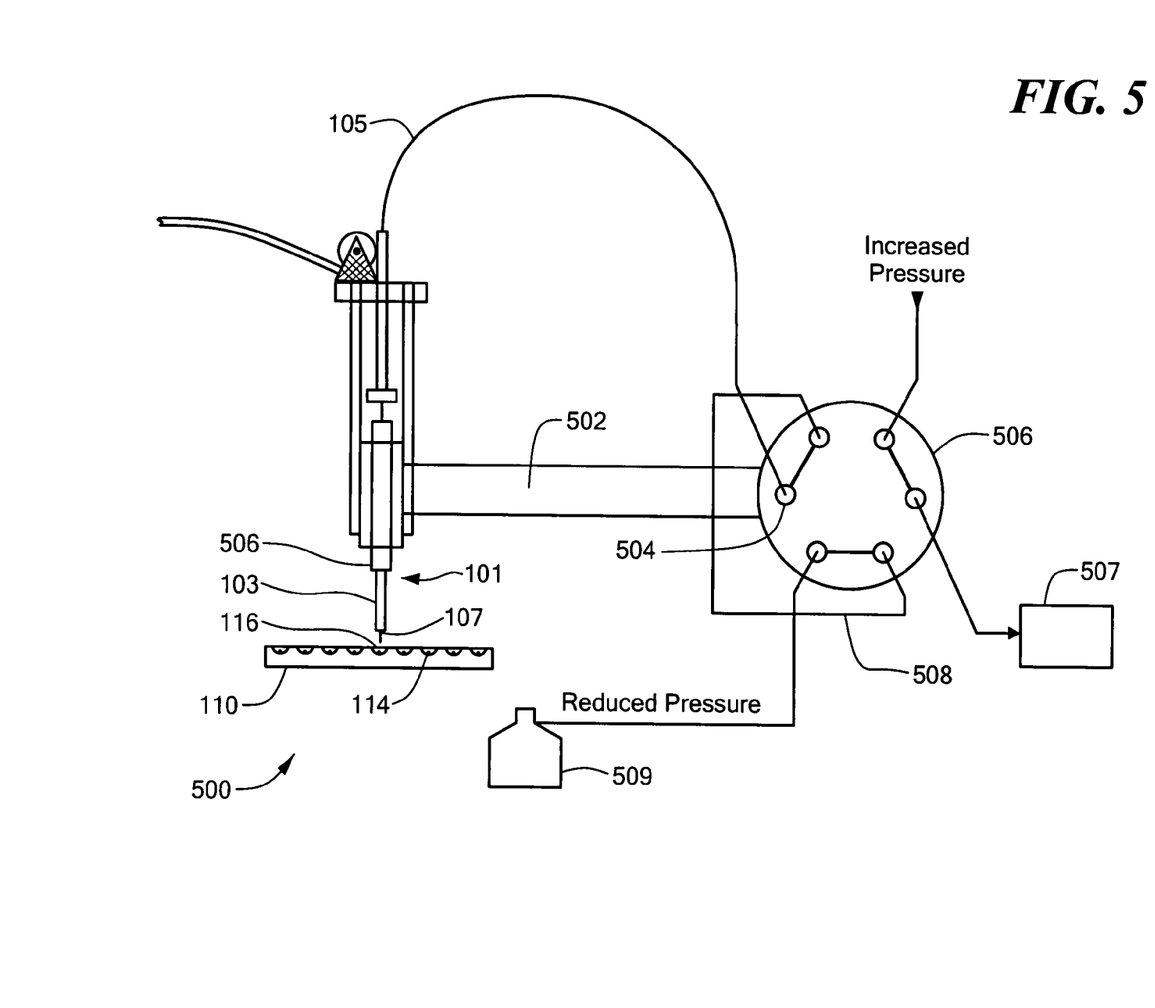
FIG. 5 is a diagram illustrating a system for aspirating a sample from a container, in accordance with an embodiment of the invention.

FIG. 5 is a diagram (not to scale) illustrating a system 500 for obtaining and aspirating a sample from a container 110, in accordance with an embodiment of the invention. The system 500 may be attached to an automated robotic motion control system, which may be controlled by a computer and related software, as known in the art. The tube assembly 101 is coupled to a mount 502 that permits motion of the tube assembly 101 relative to the container 110. Note that in various embodiments, the tube assembly 101 may be capable of motion and/or the container 110 may be capable of motion. The inner tube 105 has a second end 504 that extends beyond a distal end 506 of the outer tube 103 and is fixed in position relative to the outer tube 103.

In various embodiments, the second end 504 of the inner tube 105 is in fluid communication with an injection valve 506. The injection valve may function, for example, as described in U.S. patent application Ser. No. 09/842,361, filed Apr. 25, 2001, entitled "System and Method for High Throughput Processing of Droplets," and U.S. patent application Ser. No. 10/267,912, filed Oct. 8, 2002, entitled "System and Method for High Throughput Screening of Droplets," the contents of which are incorporated herein by reference.

The inner tube 105 is made of a flexible and resilient material, and is capable of moving freely within the outer tube 103. The inner tube 105, in a resting state, protrudes through the proximal end 107 of the outer tube, such that the tube assembly 101 is in the transmission position. The resiliency of the inner tube 105 provides a mechanical bias in the transmission position. As the tube assembly 101 is lowered towards the container 110, the inner tube 105 makes contact with the seal 112. The inner tube 105 is consequently pushed upwards, overcoming the resiliency of the inner tube 105, such that the tube assembly 101 is placed in the piercing position. This may cause, for example, a portion of the inner tube 105 positioned between the distal end 506 of the outer tube 103 and the second end 504 of the inner tube 105 to flex.

When the tube assembly 101 is sufficiently lowered, the proximal end 107 of the outer tube 103 makes contact with the seal 116, and pierces through, the seal 116. Once the seal 116 is pierced, the tension that was built up in the inner tube 105 is released and the tube assembly 101 returns to the resting state/transmission position. Upon the inner tube 105 making contact with the sample 114, the sample 114 is aspirated through the inner tube 105 for further processing.

The resiliency of the inner tube 105 is a key consideration. For example, if the inner tube 105 is too flexible and lacks sufficient resiliency, the inner tube 105 will simply flex and not return to the transmission position upon piercing of the seal 116. Examples of tubing that would be too flexible, yet chemically acceptable, include many kinds of Teflon tubing. Furthermore, certain materials may be too brittle and would break upon contacting the seal 116, such as a fused silica tubing. Plastic materials that work well for the inner tube 105 include, without limitation, polymide tubing and Poly Ether Ether Ketone (PEEK) tubing of the appropriate diameters. Tubing made from these materials have exceptionally low carryover of even very highly hydrophobic compounds, can resist high pressures before failing and can be manufactured in the 20–300 micrometer inner diameters that are optimum for minimizing linear diffusion. In other embodiments, the inner tube 105 may include a combination of materials, such as a fused silica tubing with a polymide sheath. In still other embodiments, the inner tube 105 may be made from a shaped memory alloy, such as nitinol, as is, or with surface chemistry as required by the specific application.

In various embodiments, a reduced pressure and an increased pressure is applied, by pumps for example, to a first port and a second port of the injection valve 506, respectively. In a first position, the injection valve 506 applies the reduced pressure to aspirate the sample 114 from the container 110 through inner tube 105 and into a sample loop 508. Enough of the sample 114 to fill sample loop 508 with a defined volume is aspirated. Any excess sample aspirated is collected in a trap 509 that may be positioned, for example, between the injection valve 506 and the reduced pressure source.

Figure 6:
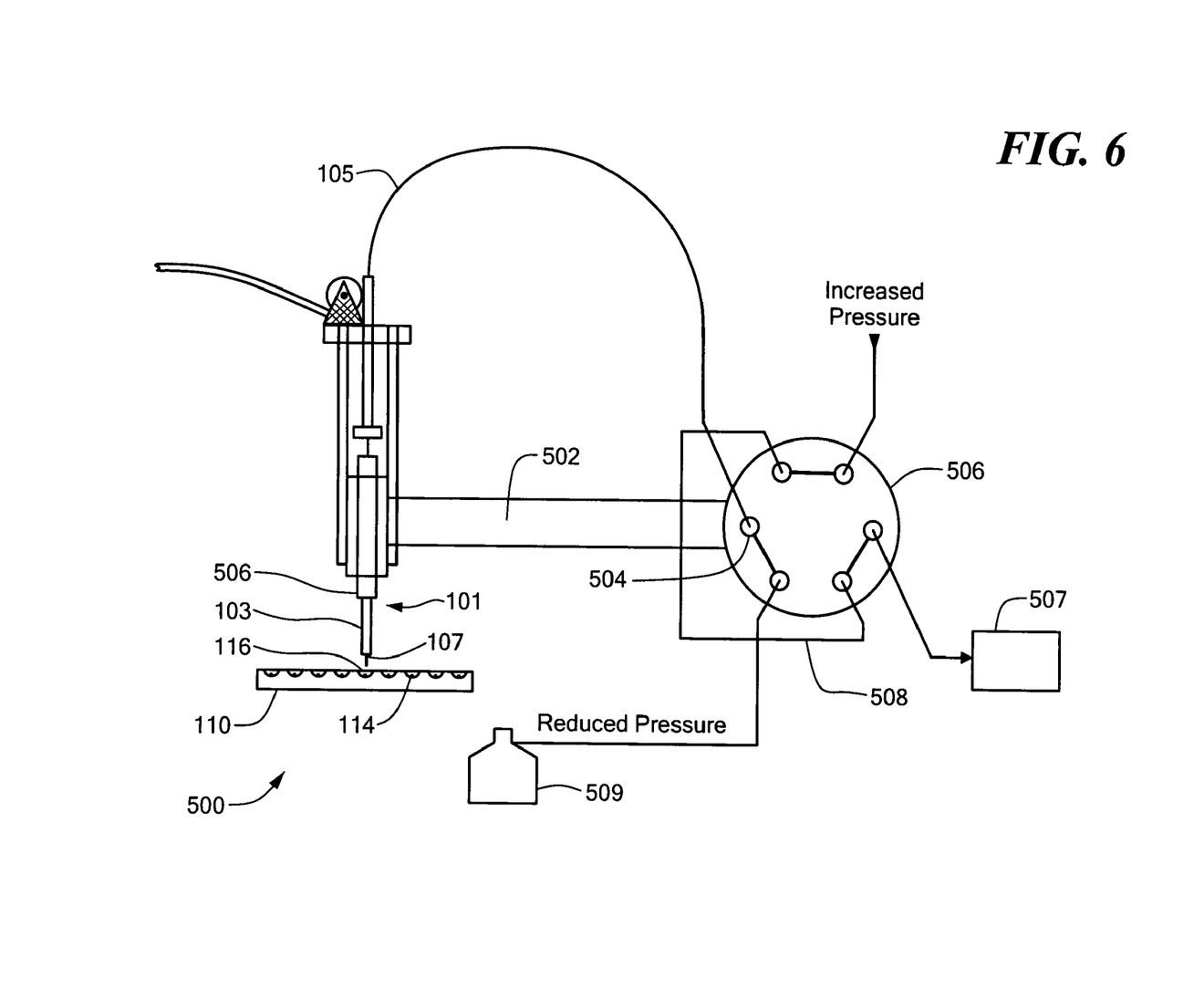
FIG. 6 is a diagram illustrating the system of FIG. 5 while the sample is being injected into a fluid circuit, in accordance with an embodiment of the invention.

Upon actuation of the injection valve 506, the metered amount of sample is introduced to a fluidic circuit 507 by applying increased pressure, as shown in FIG. 6. The amount of sample to be injected can thus be controlled by the size of the sample loop 508. The fluidic circuit 507 may include, for example, an analyzer such as a chromatography column or a mass spectrometer. The sample may be presented to the analyzer using a variety of standard systems, including atmospheric pressure chemical ionization (APCI) or electrospray ionization (ESI).

To clean the inner tube 105 prior to deactivation of valve 506 and aspiration of the next sample, the inner tube 105 may be dipped into a wash solvent or buffer solution, and the reduced pressure is applied to aspirate wash solvent through the inner tube 105 and into trap 109. Thus, the combination of the constant negative pressure and the in-line trap eliminates the need for repetitive aspiration and dispensing of wash solution through a syringe.

In various embodiments, the disclosed system and method may be implemented as a computer program product for use with a computer system. Such implementation may include a series of computer instructions fixed either on a tangible medium, such as a computer readable media (e.g., a diskette, CD-ROM, ROM, or fixed disk) or transmittable to a computer system, via a modem or other interface device, such as a communications adapter connected to a network over a medium. Medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable media with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A system for obtaining a fluidic sample from a container, the container defining a volume for holding the sample, the volume closed by a seal, the system comprising:
    an outer tube having a proximal end and a distal end, the proximal end shaped to permit piercing the seal; and
    an inner tube having an end region axially movable within the outer tube between a piercing position, wherein an end of the inner tube in the end region is retracted from the proximal end of the outer tube, and a transmission position, wherein the end of the inner tube extends axially beyond the proximal end of the outer tube, the inner tube being resilient so as to cause the inner tube to be mechanically biased in the transmission position, such bias being normally overcome while the outer tube is used to pierce the seal;
    wherein the outer tube and the inner tube form a tube assembly; and
    wherein at least one of the tube assembly and the container can be moved to cause the outer tube to pierce the seal and, after the seal is pierced, the inner tube can be used in the transmission position to permit fluid transfer with respect to the volume.

2. The system according to claim 1, wherein when inner tube is in the transmission position, the tube assembly can be moved relative to the container so as to cause the end of the inner tube to make contact with the seal and move the inner tube into the piercing position.

3. The system according to claim 1, wherein when the inner tube is in the piercing position, the inner tube returns to the transmission position after the seal is pierced due to the mechanical bias.

4. The system according to claim 1, wherein the second end of the inner tube extends beyond the distal end of the outer tube, and wherein a portion of the inner tube positioned between the distal end of the outer tube and the second end of the inner tube flexes when in the inner tube is in the piercing position.

5. The system according to claim 1, wherein the inner tube is capable of moving freely within the outer tube.

6. The system according to claim 1, further including a source of suction in fluid communication with the inner tube, the source of suction for aspirating the sample.

7. The system according to claim 6, further including an injection valve in fluid communication with the inner tube, the injection valve capable of selectively placing the source of suction in fluid communication with the inner tube.

8. The system according to claim 6, further comprising an analyzer for determining a characteristic of the sample aspirated from the container.

9. The system according to claim 8, wherein the analyzer is one of a chromatography column and a mass spectrometer.

10. The system according to claim 1, wherein the outer tube and inner tube are concentric.

11. The system according to claim 1, wherein the outer tube is made of one of a metal and a metal alloy.

12. The system according to claim 1, wherein the inner tube is made of a resilient material.

13. The system according to claim 1, wherein the inner tube is made of plastic.

14. The system according to claim 1, wherein the inner tube is made of at least one of the materials chosen from the group of material consisting of nitinol, polymide and Poly Ether Ether Ketone (PEEK).

15. The system according to claim 1, wherein the inner tube is made of fused silica with a polymide sheath.

16. The system according to claim 1, wherein the container is a microplate, the microplate including a plurality of wells, each well for holding a sample and closed by a seal.

17. The system according to claim 1, further comprising a controller for controlling movement of at least one of the tube assembly and the container.

18. The system according to claim 1, further comprising a mount that permits motion of the tube assembly relative to the container.

19. A method for obtaining a fluidic sample from a sealed container using a tube assembly, the container defining a volume for holding the sample, the volume closed by a seal, the tube assembly including an outer tube having a proximal end shaped to permit piercing the seal, the tube assembly further including a resilient inner tube having an end region axially movable within the outer tube, the method comprising:

flexing a portion of the inner tube to place the inner tube in a piercing position, wherein an end of the inner tube is retracted from the proximal end of the outer tube;

piercing the seal with the proximal end of the outer tube; and placing the inner tube in a transmission position, wherein an end of the inner tube in the end region extends axially beyond the proximal end of the outer tube.

20. The method according to claim 19, further comprising applying a source of suction to the inner tube to aspirate the sample fluid from the volume.

21. The method according to claim 20, further comprising analyzing the aspirated sample fluid.

22. The method according to claim 21, wherein analyzing includes one of chromatography and mass spectrometry.

23. The method according to claim 20, wherein applying a source of suction to the inner tube includes applying a source of suction to the inner tube via an injection valve.

24. The method according to claim 20, wherein the container is a microplate that includes a plurality of wells, each well for holding a sample and closed by a seal, the method further comprising moving at least one of the tube assembly and the container so as to aspirate sample from each well.

25. The method according to claim 19, wherein the inner tube is mechanically biased in the transmission position, and wherein placing the inner tube in the piercing position includes overcoming the mechanical bias.

26. The method according to claim 19 wherein placing the inner tube in the transmission position includes returning the inner tube to the transmission position due to the resiliency of the inner tube.

27. The method according to claim 19, wherein placing the inner tube in the piercing position includes moving at least one of the tube assembly and the container such that the end of the inner tube contacts the seal and moves into the piercing position.

* * * * *